United States Patent [19]

Savu

[11] Patent Number: 5,550,273

[45] Date of Patent: Aug. 27, 1996

[54] PROCESS FOR PREPARING FLUOROCARBON FLUOROALKANESULFONATES

[75] Inventor: Patricia M. Savu, Maplewood, Minn.

[73] Assignee: Minnesota Mining and Manufacturing Company, St. Paul, Minn.

[21] Appl. No.: 341,448

[22] Filed: Nov. 16, 1994

Related U.S. Application Data

[63] Continuation of Ser. No. 129,259, Sep. 30, 1993, abandoned.

[51] Int. Cl.$^6$ .................. C07C 309/65; C07C 309/71; C07C 309/68; C07C 309/69
[52] U.S. Cl. .................. 558/54; 558/52; 558/51; 558/48; 558/47; 558/46
[58] Field of Search .................. 558/54, 52, 51, 558/48, 47, 46

[56] References Cited

U.S. PATENT DOCUMENTS

| | | |
|---|---|---|
| 2,559,628 | 7/1951 | Joyce . |
| 2,666,797 | 1/1954 | Husted et al. . |
| 2,732,398 | 1/1956 | Brice et al. . |
| 3,293,306 | 12/1966 | Bleu et al. . |
| 3,419,595 | 12/1968 | Hansen . |
| 3,574,770 | 4/1971 | Stump et al. . |
| 4,156,791 | 5/1979 | Childs . |
| 5,062,691 | 11/1991 | Tristani-Kendra et al. .............. 359/56 |

FOREIGN PATENT DOCUMENTS

| | | |
|---|---|---|
| 2440272 | 3/1976 | Germany . |
| 2065112 | 6/1981 | United Kingdom ............ C07C 19/08 |

OTHER PUBLICATIONS

Abe, T. et al., "Electrochemical Fluorination (Simons Process) as a Route to Perfluorinated Organic Compounds of Industrial Interest," in *Preparation, Properties, and Industrial Applications of Organofluorine Compounds*, R. E. Banks (editor), p. 37, Ellis Howard (1982).
Coffman and Raasch, J. Org. Chem. 14, 747 (1949).
DeVries, V. G. et al., J. Med. Chem. 26, 1411–21 (1984).
Gassman, P. G. et al., J. Org. Chem. 1984, 49, 2258–73.
Hazeltine, R. N. et al., J. Chem. Soc. 1955, 2901.
Huang, W. Y., J. Fluorine Chem. 32, 179 (1986).
Knunyants, I. L. et al. in Advances in Chem. (Uspekhi Khimi) 32, 461 (English translation) (1963).
LaZerte and Koshar, J. Am. Chem. Soc., 77, 910 (1955).
McBee, E. T. et al., J. Am. Chem. Soc. 74, 444 (1952).
Sakamoto, S. et al., J. Antibiotics 37 (12), 1628–34 (1984).
Stang, P. J. et al., Synthesis 1982, 85.
Trott, P. W. et al., 126th National Meeting of the American Chemical Society, abstract, p. 42–M, New York, N.Y. (1954).
Weiyuan, H. et al., Chemistry 2, 31 (1987).

Primary Examiner—Nicky Chan
Attorney, Agent, or Firm—Gary L. Griswold; Walter N. Kirn; Lucy C. Weiss

[57] ABSTRACT

A process for preparing fluorocarbon fluoroalkanesulfonates comprises (a) forming a mixture comprising at least one fluoroalkanesulfonyl halide, e.g., perfluoromethanesulfonyl fluoride, at least one fluorocarbon-substituted carbinol, e.g., 1,1-dihydroperfluorobutoxyethoxyethanol, and at least one base, e.g., triethyl amine; and (b) allowing the mixture to react in the absence of solvent at a temperature below ambient. The process is volume-efficient and provides high yields of fluorocarbon fluoroalkanesulfonates useful as intermediates in, e.g., drug synthesis.

17 Claims, No Drawings

PROCESS FOR PREPARING FLUOROCARBON FLUOROALKANESULFONATES

This is a continuation of application Ser. No. 08/129,259 filed Sep. 30, 1993, now abandoned.

FIELD OF THE INVENTION

This invention relates to a process for preparing fluorocarbon fluoroalkanesulfonate esters, e.g., 1,1-dihydroperfluorobutoxyethoxyethyl perfluoromethanesulfonate.

BACKGROUND OF THE INVENTION

Fluorocarbon fluoroalkanesulfonate esters have utility as intermediates, e.g., in the synthesis of drugs such as antibiotics (see, e.g., S. Sakamoto et al., J. Antibiotics 37 (12), 1628–34 (1984)). These compounds have often been prepared by the reaction of a fluoroalkanesulfonic anhydride with a fluorine-containing alcohol in the presence of a base such as pyridine, as described, e.g., by P. G. Gassman et al., J. Org. Chem. 1984, 49, 2258–73 (at page 2270).

Fluorocarbon fluoroalkanesulfonates have also been prepared by reaction of a fluoroalkanesulfonyl halide (rather than the corresponding anhydride) with a fluorine-containing alcohol in the presence of base, as described, e.g., by Sakamoto et al., supra, at page 1631, by V. G. DeVries et al., J. Med. Chem. 26, 1411–21 (at page 1417)(1983), and in U.S. Pat. No. 3,419,595 (Hansen). These references disclose the general use of a solvent such as methylene chloride and the use of various different reaction temperatures.

SUMMARY OF THE INVENTION

Briefly, in one aspect, this invention provides a process for preparing fluorocarbon fluoroalkanesulfonates. The process comprises (a) forming a mixture comprising at least one fluoroalkanesulfonyl halide, e.g., perfluoromethanesulfonyl fluoride, at least one fluorocarbon-substituted carbinol, e.g., 1,1-dihydroperfluorobutoxyethoxyethanol, and at least one base, e.g., triethyl amine; and (b) allowing the mixture to react in the absence of solvent at a temperature below ambient. The mixture is preferably allowed to react at a temperature in the range of from about −40° C. to about +15° C. As used herein, the term fluorocarbon includes fluoroalkyl, fluorocycloalkyl, and fluoroether groups.

The process of the invention utilizes fluoroalkanesulfonyl halides, rather than the higher cost anhydrides, and surprisingly provides fluorocarbon fluoroalkanesulfonates in higher yield (and with greater volume efficiency and therefore lower cost) than the traditional halide process employing solvent and/or higher reaction temperatures. Since no solvent is utilized, there is no need for a solvent-stripping step (with its accompanying time and cost), and the potential for reducing yields by removing low-boiling product along with the solvent is thereby eliminated.

DETAILED DESCRIPTION OF THE INVENTION

Fluoroalkanesulfonyl halides suitable for use in the process of the invention can be represented by the general formula $R_fSO_2X$, where $R_f$ is selected from the group consisting of perfluorinated alkyl groups having from 1 to about 10 carbon atoms, partially-fluorinated alkyl groups having from 1 to about 10 carbon atoms, unsubstituted or perfluoroalkyl-substituted perfluorocycloalkyl groups having from 4 to about 8 carbon atoms, and unsubstituted or perfluoroalkyl-substituted, partially-fluorinated cycloalkyl groups having from 4 to about 8 carbon atoms; and X is selected from the group consisting of fluorine, chlorine, bromine, and iodine. Preferably, X is fluorine or chlorine.

The perfluorinated alkanesulfonyl fluorides (and, indirectly, the chlorides) are readily available by the electrochemical fluorination of the corresponding alkanesulfonyl fluorides, as described in U.S. Pat. No. 2,732,398 (Brice et al.), the description of which is incorporated herein by reference. (See also P. W. Trott et al., 126th National Meeting of the American Chemical Society, abstract at page 42-M, New York, N.Y. (1954).) Perfluorooctanesulfonyl fluoride is also commercially available from 3M Co. under the tradename Fluorad™ fluorochemical sulfonyl fluoride FX-8. Routes to perfluoroalkanesulfonyl chlorides are described by P. J. Stang et al. in Synthesis 1982, 85 and by R. N. Hazeltine et al. in J. Chem. Soc. 1955, 2901. The chlorides of the ω-hydroperfluorinated acids are described by Coffman and Raasch in J. Org. Chem. 14, 747 (1949), by H. Weiyuan et al. in Chemistry 2, 31 (1987), and by W. Y. Huang, J. Fluorine Chem. 32, 179 (1986).

Representative examples of fluoroalkanesulfonyl halides suitable for use in the process of the invention include $CF_3SO_2F$, $CF_3SO_2Cl$, $C_4F_9SO_2F$, $C_4F_9SO_2Cl$, $C_8F_{17}SO_2F$, $C_8F_{17}SO_2Cl$, $C_8F_{17}SO_2Br$, $C_8F_{17}SO_2I$, $C_{10}F_{21}SO_2F$, $C_{10}F_{21}SO_2Cl$, cyclo-$(C_6F_{11})SO_2F$, cyclo-$(C_6F_{11})SO_2Cl$, $C_2F_5$-cyclo-$(C_6F_{10})SO_2F$, $C_2F_5$-cyclo-$(C_6F_{10})SO_2Cl$, $H(CF_2)_2SO_2Cl$, $H(CF_2)_4SO_2Cl$, $H(CF_2)_8SO_2Cl$, $H(CF_2)_{10}SO_2Cl$, $H(CF_2)_4SO_2F$, and $H(CF_2)_8SO_2F$. Preferably, perfluoroalkanesulfonyl fluorides and chlorides are utilized, most preferably, perfluoromethanesulfonyl fluoride and perfluorobutanesulfonyl fluoride because of their high yields from the electrochemical fluorination process and correspondingly low costs (see, e.g., T. Abe et al., "Electrochemical Fluorination (Simons Process) as a Route to Perfluorinated Organic Compounds of Industrial Interest," in *Preparation, Properties, and Industrial Applications of Organofluorine Compounds*, R. E. Banks (editor), page 37, Ellis Howard (1982)).

Fluorocarbon-substituted carbinols suitable for use in the process of the invention can be represented by the general formula $R_f'$—$CH_2$—OH, where $R_f'$ is selected from the group consisting of —D—$R_f^a$ and —D—$R_f^b$—$R_h$, where D is selected from the group consisting of a covalent bond,

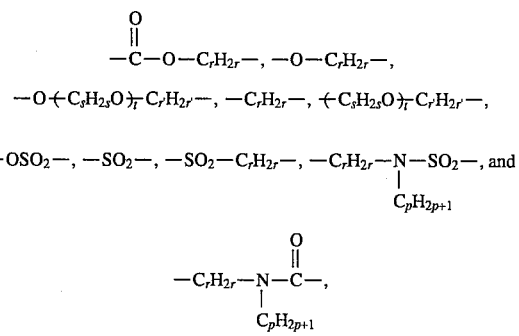

where r and r' are independently integers of 1 to about 20, s is independently an integer of 1 to about 10 for each $(C_sH_{2s}O)$, t is an integer of 1 to about 6, and p is an integer of 0 to about 4; $R_f^a$ is selected from the group consisting of —$(C_xF_{2x}O)_zC_yF_{2y+1}$, —$C_qF_{2q}X$, and —$C_qF_{2q-2}X$, preferably —$(C_xF_{2x}O)_zC_yF_{2y+1}$, where x is independently an integer of 1 to about 10 (preferably 1 to about 4) for each $C_xF_{2x}O$ group, y is an integer of 1 to about 10 (preferably 1 to about 6), z is an integer of 1 to about 10 (preferably 1 to about 3), q is an integer of 1 to about 20, and X is selected from the group consisting of hydrogen and fluorine; $R_f^b$ is a linear or branched, perfluorinated or partially-fluorinated alkylene group having from 1 to about 10 carbon atoms (preferably, from about 2 to about 6 carbon atoms) and optionally containing one or more catenary ether oxygen atoms; and $R_h$ is a linear or branched alkyl group having from 1 to about 14 carbon atoms (preferably, from about 3 to about 10 carbon atoms) and optionally containing one or more catenary ether oxygen atoms. Preferably, $R_f^b$ is perfluorinated, both $R_h$ and $R_f^b$ are linear, and $R_h$ contains one or two catenary ether oxygen atoms. The fluorocarbon-substituted carbinols, as well as the above-described fluoroalkanesulfonyl halides, can contain small amounts of chlorine, i.e., carbon-bonded chlorine atoms.

In general, the fluorocarbon-substituted carbinols of the formula $R_f'$—$CH_2$—OH can be obtained by reduction of the corresponding carboxylic acid with lithium aluminum hydride or by catalytic hydrogenation over a copper-chromium oxide catalyst (as described in U.S. Pat. No. 2,666,797 (Husted et al.), the description of which is incorporated herein by reference), by sodium borohydride reduction of the methyl ester of the corresponding fluorinated carboxylic acid (as described in U.S. Pat. No. 4,156,791 (Childs), the description of which is incorporated herein by reference, and by I. L. Knunyants et al. in Advances in Chem. (Uspekhi Khimi) 32, 461 (English translation) (1963)), and by sodium borohydride reduction of the corresponding fluorinated carboxylic acid halide (as described in U.S. Pat. Nos. 3,293,306 (Bleu et al.) and 3,574,770 (Stump et al.), the descriptions of which are incorporated herein by reference). See also E. T. McBee et al., J. Am. Chem. Soc. 74, 444 (1952). Suitable trihydroperfluoroalkanols are available by the free radical addition of methanol to perfluoroolefins, e.g., $CF_3CF=CF_2$ and $C_5F_{11}CF=CF_2$, as described by LaZerte and Koshar in J. Am. Chem. Soc., 77, 910 (1955), or by free radical telomerization of tetrafluoroethylene with methanol, as described in U.S. Pat. No. 2,559,628 (Joyce), the description of which is incorporated herein by reference.

Representative examples of fluorocarbon-substituted carbinols suitable for use in the process of the invention include $CF_3CH_2OH$, $CF_3CF_2CH_2OH$, $CF_3(CF_2)_2CH_2OH$, $CF_3(CF_2)_4CH_2OH$, $CF_3(CF_2)_6CH_2OH$, $CF_3(CF_2)_3OCF_2CF_2OCF_2CH_2OH$, $CF_3O(CF_2CF_2O)_2CF_2CH_2OH$, $C_4F_9O(CF_2CF_2O)_2CF_2CH_2OH$, $C_6F_{13}O(CF_2CF_2O)_2CF_2CH_2OH$, $CF_3(CF_2)_5OCF_2CF_2OCF_2CH_2OH$, $CF_3(CF_2)_3OCF_2CF_2O(CF_2)_3CH_2OH$, $CF_3(CF_2)_3O(CF_2CF_2O)_2(CF_2)_3CH_2OH$, $CF_3(CF_2)_3O(CF_2)_4O(CF_2)_3CH_2OH$, $C_4H_9OCH_2(CF_2)_3CH_2OH$, $C_2H_5OCH_2(CF_2)_3CH_2OH$, and $CH_3OCH_2(CF_2)_3CH_2OH$. Fluoroether-substituted carbinols are preferred.

Bases suitable for use in the process of the invention are those organic bases which have a base strength comparable to that of triethyl amine. Representative examples of suitable bases include tertiary amines, e.g., trimethyl amine, triethyl amine, tripropyl amine, tributyl amine, N,N-diisopropylethyl amine, N-methyl morpholine, N-ethyl morpholine, N-propyl morpholine, and 1-methylpyrrolidone. Preferably, triethyl amine, tributyl amine, N,N-diisopropylethyl amine, and N-methyl morpholine are used in the process of the invention, as these bases are readily available, inexpensive, and liquid at room temperature. Most preferably, triethyl amine is utilized.

The process of the invention can be carried out by combining at least one fluoroalkanesulfonyl halide, at least one fluorocarbon-substituted carbinol, and at least one base in a temperature- and/or pressure-controlled vessel, so as to form a mixture thereof. The mixture is preferably protected from atmospheric moisture either under a dry, inert atmosphere or by evacuation and sealing of the vessel. Generally, stoichiometric amounts of the components of the mixture can be utilized, but a slight excess of both base and halide can also be useful. Thus, up to an essentially stoichiometric amount of carbinol can be utilized. The components can be individually added to the vessel in any order, can be added simultaneously, or can be added in any manner of combination. However, a temperature below ambient is preferably achieved (e.g., by cooling the vessel) prior to the start of reaction (i.e., prior to addition of the third component of the mixture) and is preferably maintained (e.g., by controlling the rate of addition of the third component) until the reaction has gone to completion (e.g., until all of the carbinol is consumed). When low molecular weight, i.e., gaseous, fluoroalkanesulfonyl halides are utilized, the carbinol(s) and the base(s) are preferably added to the vessel first, so that the temperature of the contents of the vessel can be easily controlled by controlling the rate of gas addition.

The mixture is preferably maintained at a temperature of from about −40° C. to about +15° C. (more preferably from about −30° C. to about +5° C., most preferably from about −20° C. to about 0° C.) and is allowed to react (preferably with stirring) in the absence of solvent. The reaction can then be quenched by the addition of water to the vessel (generally, in an amount sufficient to dissolve the hydrohalide reaction product). Preferably, the desired fluorocarbon fluoroalkanesulfonate product is recovered from the resulting reaction mixture, e.g., by separation of the resulting fluorochemical layer from the resulting aqueous layer, followed by an acid wash and distillation of the separated fluorochemical layer.

The process of the invention provides fluorocarbon fluoroalkanesulfonate esters of the formula $R_f'$—$CH_2$—O—$SO_2$—$R_f$ (where $R_f'$ and $R_f$ are as defined above) in higher yield and with greater volume efficiency (and therefore lower cost) than the traditional halide process employing solvent and/or higher reaction temperatures. These esters are useful as intermediates, e.g., in drug synthesis.

This invention is further illustrated by the following examples, but the particular materials and amounts thereof recited in these examples, as well as other conditions and details, should not be construed to unduly limit this invention.

EXAMPLES

Example 1

Preparation of Undecafluorohexyl Perfluoromethanesulfonate ($C_5F_{11}CH_2OSO_2CF_3$)

Undecafluorohexanol (64.8 g, 0.216 mole) and triethyl amine (31.5 g, 0.31 mole) were mixed together in a flask fitted with a −78° finger condenser, a thermometer, a dip tube for gas addition, and an overhead stirrer. The system was purged with dry nitrogen and then kept under slight nitrogen pressure. With good stirring, the flask was cooled to an internal temperature of −14° C. At this time, the nitrogen was shut off, and addition of perfluoromethanesulfonyl fluoride (PMSF) was begun. Over a period of one hour, 53 g of PMSF (91%, 0.32 mole) was added, and the internal temperature was kept between −10° C. and −14° C. The reaction mixture was then stirred under slight nitrogen pressure for four hours, eventually warming to 4° C. At this time, 64 ml of water was slowly added to the mixture. The resulting fluorochemical layer was separated from the resulting aqueous layer and weighed (92.7 g). The separated fluorochemical layer was washed with 67 ml of 10% sulfuric acid and 64 ml of water; 91.2 g of product was obtained. Gas chromatographic analysis of the washed fluorochemical layer showed it to contain 0.2 area % of a low boiling material previously identified as $C_5F_{11}CH_2F$. The washed fluorochemical layer was distilled at reduced pressure (35 mm) at a head temperature of 76°–81° C. to give 84.5 g of the desired perfluoromethanesulfonate (91% yield).

Example 2

Preparation of Undecafluorohexyl Perfluoromethanesulfonate ($C_5F_{11}CH_2OSO_2CF_3$) at a Higher Temperature The procedure of Example 1 was carried out using 385 g of undecafluorohexanol, 218 g of triethyl amine, and 333 g of PMSF, except that the reaction temperature during the PMSF addition was 10° C. and the reaction was allowed to stir at room temperature overnight with warming. The weight of the crude fluorochemical product obtained after washing but before distillation was 525 g. Gas chromatographic analysis of the crude washed product showed it to contain 10.8 area % of a low boiling material previously identified as $C_5F_{11}CH_2F$. Distillation of the crude washed product gave 473 g of the desired perfluoromethanesulfonate (82% yield).

Example 3

Preparation of Pentadecafluorooctyl Perfluoromethanesulfonate ($C_7F_{15}CH_2OSO_2CF_3$)

Following essentially the procedure of Example 1, 810 g pentadecafluorooctanol, 214 g of triethyl amine, and 325 g of 99% PMSF were reacted to give crude fluorochemical product. After addition of the PMSF, the reaction temperature was kept between −22° C. and 0° C. and then was allowed to warm up to 0° C. prior to the addition of water. The crude product was washed with 800 ml of water, then with 800 ml of 3.5% HCl, and then with 800 ml of water, to yield 1061 g of crude, washed product. The washed product was distilled at a pressure of 1.5 mm and a head temperature of 60°–67° C. to give 1010 g of pentadecafluorooctyl perfluoromethanesulfonate (94% yield).

Example 4

Preparation of 1,1-Dihydroperfluorobutoxyethoxyethyl Perfluoromethanesulfonate ($C_4F_9OCF_2CF_2OCF_2CH_2OSO_2CF_3$)

Following essentially the procedure of Example 1, 650 g 1,1-dihydroperfluorobutoxyethoxyethanol, 204 g of triethyl amine, and 345 g of 91% PMSF were reacted to give crude fluorochemical product. After addition of the PMSF, the reaction temperature was kept between −22° C. and 0° C. and then was allowed to warm up to 0° C. prior to the addition of water. The crude product was washed with 360 ml of water, then with 360 ml of 3.5% HCl, and then with 360 ml of water, to yield 872 g of crude, washed product. The washed product was distilled at a pressure of 3.5 mm and a head temperature of 61°–78° C. to give 772 g of 1,1-dihydroperfluorobutoxyethoxyethyl perfluoromethanesulfonate (92% yield).

Example 5

Preparation of 1,1-Dihydroperfluorohexoxyethoxyethyl Perfluoromethanesulfonate ($C_6F_{13}OCF_2CF_2OCF_2CH_2OSO_2CF_3$)

Following essentially the procedure of Example 1, 130 g 1,1-dihydroperfluorohexoxyethoxyethanol, 25.8 g of triethyl amine, and 39 g of 99% PMSF were reacted to give crude fluorochemical product. After addition of the PMSF, the reaction temperature was kept between −22° C. and 0° C. and then was allowed to warm up to 0° C. prior to the addition of water. The crude product was washed with 100 ml of water, then with 100 ml of 3.5% HCl, and then with 100 ml of water, to yield 156 g of crude, washed product. The washed product was distilled at a pressure of 3.5 mm and a head temperature of 80°–85° C. to give 142.8 g of 1,1-dihydroperfluorohexoxyethoxyethyl perfluoromethanesulfonate (88% yield).

Example 6

Preparation of 1,1-Dihydroperfluoromethoxyethoxyethoxyethyl Perfluoromethanesulfonate ($CF_3O(CF_2CF_2O)_2CF_2CH_2OSO_2CF_3$)

Following essentially the procedure of Example 1, 695 g of 1,1-dihydroperfluoromethoxyethoxyethoxyethanol, 185 g of triethyl amine, and 279 g of 91% PMSF were reacted to give crude fluorochemical product. After addition of the PMSF, the reaction temperature was kept between −22° C. and 0° C. and then was allowed to warm up to 0° C. prior to the addition of water. The crude product was washed with 700 ml of water, then with 700 ml of 3.5% HCl, and then with 700 ml of water, to yield 905 g of crude, washed product. The washed product was distilled at a pressure of 1.5 mm and a head temperature of 68°–78° C. to give 831 g of 1,1-dihydroperfluoromethoxyethoxyethoxyethyl perfluoromethanesulfonate (90% yield).

Example 7

Preparation of 5-Butoxy-2,2,3,3,4,4-hexafluoropentyl Perfluoromethanesulfonate ($C_4H_9OCH_2(CF_2)_3CH_2OSO_2CF_3$)

Following essentially the procedure of Example 1, 88 g of 5-butoxy-2,2,3,3,4,4-hexafluoropentanediol ($C_4H_9OCH_2(CF_2)_3CH_2OH$), 47.9 g of triethyl amine, and 81 g of 99% PMSF were reacted to give crude fluorochemical product. After addition of the PMSF, the reaction temperature was kept between −22° C. and 0° C. and then was allowed to warm up to 0° C. prior to the addition of water. The crude product was washed with 90 ml of water, then with 90 ml of 3.5% HCl, and then with 90 ml of water, to yield 145 g of crude, washed product. The washed product was distilled at a pressure of 3.0 mm and a head temperature of 91°–95° C. to give 114 g of 5-butoxy-2,2,3,3,4,4-hexafluoropentanediol perfluoromethanesulfonate (87% yield).

Example 8

Preparation of 1,1-Dihydroperfluorobutoxybutoxybutyl Perfluoromethanesulfonate ($C_4F_9O(CF_2)_4O(CF_2)_3CH_2OSO_2CF_3$)

Following essentially the procedure of Example 1, 103 g 1,1-dihydroperfluorobutoxybutoxybutanol, 17.2 g of triethyl amine, and 26 g of 99% PMSF were reacted to give crude fluorochemical product. After addition of the PMSF, the reaction temperature was kept between −22° C. and 0° C. and then was allowed to warm up to 0° C. prior to the addition of water. The crude product was washed with 100 ml of water, then with 50 ml of 3.5% HCl, and then with 50 ml of water, to yield 120 g of crude, washed product. The product was distilled at a pressure of 0.1 mm and a head temperature of 71°–80° C. to give 114 g of 1,1-dihydroperfluorobutoxybutoxybutyl perfluoromethanesulfonate (92% yield).

Example 9

Preparation of 1,1-Dihydroperfluoro-4-(hexoxyethoxy)ethyl Nonafluorobutanesulfonate ($C_6F_{13}O(CF_2)_2OCF_2CH_2OSO_2C_4F_9$)

1,1-Dihydroperfluoro-2-(hexoxyethoxy)ethanol (bp 80°–85° C. at 3.5 mm Hg) was prepared by sodium borohydride reduction of its corresponding methyl ester. 1,1-Dihydroperfluoro-2-(hexoxyethoxy)ethanol (100 g, 98 wt %) was dissolved in 22 g of triethyl amine and placed in a flask fitted with a magnetic stirrer, a thermometer, and an addition funnel. Under a stream of dry nitrogen, the flask was cooled in a bath of water/methanol/dry ice to −30° C. Over a period of ten minutes, nonafluorobutanesulfonyl fluoride (65 g) was added to the rapidly-stirred flask. After the addition of the sulfonyl fluoride, the resulting mixture was allowed to warm up to 0° C. and was stirred for two hours. After 10 minutes, the clear yellow solution began to cloud up with triethyl ammonium fluoride. After two hours, 100 g of water was rapidly added to the mixture with stirring. The resulting yellow fluorochemical layer was separated from the resulting aqueous layer to give 159 g of crude fluorochemical product. The crude fluorochemical product was then washed with 100 g of 3.5% HCl and 100 g of water, and 148 g of fluorochemical product was obtained. The washed product was distilled at a pressure of 0.01 mm and a head temperature of 85°–87° C. to give 132.9 g of the desired nonafluorobutanesulfonate product (88% yield), as confirmed by infrared analysis.

Example 10

Preparation of 1,1-Dihydroperfluorobutoxyethoxyethyl Perfluorooctanesulfonate ($C_4F_9O(CF_2)_2OCF_2CH_2OSO_2C_8F_{17}$)

Following essentially the procedure of Example 9, 50 g (0.115 mole) 1,1-dihydroperfluorobutoxyethoxyethanol, 13 g of triethyl amine, and 65 g (0.126 mole) of perfluorooctanesulfonyl fluoride were reacted to give crude fluorochemical product. After addition of the perfluorooctanesulfonyl fluoride, the reaction temperature was kept between −30° C. and 0° C. and then was allowed to warm up to 0° C. prior to the addition of water. The crude product was washed with 100 ml of water, then with 100 ml of 3.5% HCl, and then with 100 ml of water, to yield 110 g of crude, washed product. The product was distilled at a pressure of 0.4 mm and a head temperature of 97° C.–110° C. to give 82 g of 1,1-dihydroperfluorobutoxyethoxyethyl perfluorooctanesulfonate (77% yield), as confirmed by infrared analysis.

Comparative Example

Preparation of 1,1-Dihydroperfluorobutoxyethoxyethyl Perfluorooctanesulfonate ($C_4F_9O(CF_2)_2OCF_2CH_2OSO_2C_8F_{17}$)

Using the procedure of Example 3 of U.S. Pat. No. 3,419,595 (Hansen), 48 g (0.096 mole) of perfluorooctanesulfonyl fluoride was added to 10 g (0.099 mole) of triethyl amine in a mechanically-agitated flask under slight positive dry nitrogen pressure. 38 g (0.088 mole) of 1,1-dihydroperfluorobutoxyethoxyethanol was added to the flask, and the reaction mixture was heated to 95°–100° C. for three hours. The mixture was cooled to room temperature and poured into 100 g of water. The resulting fluorochemical layer was separated from the resulting aqueous layer, and the separated fluorochemical layer was washed with 100 ml of 3.5% HCl and then with 100 ml of water. Gas chromatographic analysis (⅛" diameter, 12 ft 3% OV-101) (50°–250° C., one min post injection interval, 20 deg/min) showed the volatile portion of the washed fluorochemical to consist of components giving the following peaks (area % (retention time)): 66.4% (2.71 min), 8.8% (3.9 min), and 18.8% (8.93 min), the latter peak being the desired perfluorooctanesulfonate product. The washed fluorochemical was distilled at atmospheric pressure, and then the pot residue was distilled at a pressure of 0.01 mm and a head temperature of 93°–97° C. to give 9.8 g of the desired product. The pot temperature was taken up to 180° C. at 0.01 mm, but no additional product distilled off. The yield of the desired product was only 12% (the major volatile product being instead $C_4F_9O(CF_2)_2OCF_2CH_2F$). This example shows that the use of reaction temperatures above ambient results in a reduced yield (12%) compared to the yield obtained by using the process of the invention (77%, as shown in Example 10).

Example 11

Preparation of Trifluoroethyl Perfluoromethanesulfonate ($CF_3CH_2OSO_2CF_3$)

Following essentially the procedure of Example 1, 100 g trifluoroethanol (1.0 mole, bp=77°–80° C.), 110 g of triethyl amine (1.09 mole), and 188 g of 91% PMSF (1.12 mole) were reacted to give crude fluorochemical product. After addition of the PMSF, the reaction temperature was kept between −22° C. and 0° C. and then was allowed to warm up to 0° C. prior to the addition of water. The crude product was washed with 250 ml of water, then with 250 ml of 3.5% HCl, and then with 250 ml of water, and 235 g of crude, washed product was obtained. Gas chromatographic analysis (⅛" diameter, 12 ft 3% OV-101) (50°–250° C., one min post injection interval, 20 deg/min) showed the washed product to consist of components giving the following peaks (area % (retention time)): 1.3% (1.32 min), 1.3% (1.65 min), and 93% (2.67 min). The washed product was one-plate distilled from 6 g of phosphorus pentoxide at atmospheric pressure and a head temperature of 87°–90° C. to give 208 g of trifluoroethyl perfluoromethanesulfonate (90% yield), as confirmed by boiling point and by gas chromatographic/mass spectrometric analysis. U.S. Pat. No. 3,419,595 (Hansen) (Example 1) reports a yield of only 74%.

Various modifications and alterations of this invention will become apparent to those skilled in the art without departing from the scope and spirit of this invention.

I claim:

1. A process for preparing fluorocarbon fluoroalkanesulfonates or fluorocarbon fluorocycloalkanesulfonates comprising (a) forming a mixture comprising at least one compound selected from the group consisting of fluoroalkanesulfonyl halides and fluorocycloalkanesulfonyl halides, up to an essentially stoichiometric amount of at least one fluorocarbon-monosubstituted carbinol, and at least one base; and (b) allowing said mixture to react in the absence of solvent at a temperature below about +15° C.

2. The process of claim 1 wherein said temperature is in the range of from about −40° C. to about +15° C.

3. The process of claim 2 wherein said range is from about −30° C. to about +5° C.

4. The process of claim 3 wherein said range is from about −20° C. to about 0° C.

5. The process of claim 1 wherein said fluoroalkanesulfonyl halide or fluorocycloalkanesulfonyl halide is represented by the general formula $R_fSO_2X$, where $R_f$ is selected from the group consisting of perfluorinated alkyl groups having from 1 to about 10 carbon atoms, partially-fluorinated alkyl groups having from 1 to about 10 carbon atoms, unsubstituted or perfluoroalkyl-substituted perfluorocycloalkyl groups having from 4 to about 8 carbon atoms, and unsubstituted or perfluoroalkyl-substituted, partially-fluorinated cycloalkyl groups having from 4 to about 8 carbon atoms; and X is selected from the group consisting of fluorine, chlorine, bromine, and iodine.

6. The process of claim 5 wherein said $R_f$ is selected from the group consisting of perfluorinated alkyl groups having from 1 to about 10 carbon atoms; and said X is selected from the group consisting of fluorine and chlorine.

7. The process of claim 6 wherein said $R_f$ is selected from the group consisting of perfluoromethyl and perfluorobutyl; and said X is fluorine.

8. The process of claim 1 wherein said fluorocarbon-monosubstituted carbinol is represented by the general formula $R_f'$—$CH_2$—OH, where $R_f'$ is selected from the group consisting of —D—$R_f^a$ and —D—$R_f^b$—$R_h$, where D is selected from the group consisting of a covalent bond,

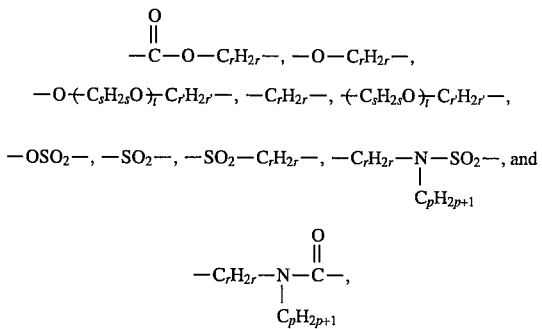

where r and r' are independently integers of 1 to about 20, s is independently an integer of 1 to about 10 for each ($C_sH_{2s}O$), t is an integer of 1 to about 6, and p is an integer of 0 to about 4; $R_f^a$ is selected from the group consisting of —($C_xF_{2x}O)_zC_yF_{2y+1}$, —$C_qF_{2q}X'$, and —$C_qF_{2q-2}X'$, where x is independently an integer of 1 to about 10 for each $C_xF_{2x}O$ group, y is an integer of 1 to about 10, z is an integer of 1 to about 10, q is an integer of 1 to about 20, and X' is selected from the group consisting of hydrogen and fluorine; $R_f^b$ is a linear or branched, perfluorinated or partially-fluorinated alkylene group having from 1 to about 10 carbon atoms and optionally containing one or more catenary ether oxygen atoms; and $R_h$ is a linear or branched alkyl group having from 1 to about 14 carbon atoms and optionally containing one or more catenary ether oxygen atoms.

9. The process of claim 8 wherein said $R_f^a$ is —($C_xF_{2x}O)_zC_yF_{2y+1}$.

10. The process of claim 8 wherein said x is independently an integer of 1 to about 4 for each $C_xF_{2x}O$ group; said y is an integer of 1 to about 6; said z is an integer of 1 to about 3; said $R_f^b$ is a linear, perfluorinated alkylene group having from about 2 to about 6 carbon atoms; and said $R_h$ is a linear alkyl group having from about 3 to about 10 carbon atoms and containing one or more catenary ether oxygen atoms.

11. The process of claim 10 wherein said fluorocarbon-monosubstituted carbinol is selected from the group consisting of undecafluorohexanol, pentadecafluorooctanol, 1,1-dihydroperfluorobutoxyethoxyethanol, 1,1-dihydroperfluorohexoxyethoxyethanol, 1,1-dihydroperfluoromethoxyethoxyethanol, 5-butoxy-2,2,3,3,4,4-hexafluoropentanediol, and 1,1-dihydroperfluorobutoxybutoxybutanol.

12. The process of claim 1 wherein said base is a tertiary amine.

13. The process of claim 12 wherein said base is selected from the group consisting of trimethyl amine, triethyl amine, tripropyl amine, tributyl amine, N,N-diisopropylethyl amine, N-methyl morpholine, N-ethyl morpholine, N-propyl morpholine, and 1-methylpyrrolidone.

14. The process of claim 13 wherein said base is selected from the group consisting of triethyl amine, tributyl amine, N,N-diisopropylethyl amine, and N-methyl morpholine.

15. The process of claim 14 wherein said base is triethyl amine.

16. The process of claim 1 further comprising the step of recovering said fluorocarbon fluoroalkanesulfonate fluorocarbon fluorocycloalkanesulfonate from the resulting reaction mixture.

17. A process for preparing fluoroether perfluoroalkanesulfonates or fluoroether perfluorocycloalkanesulfonates comprising (a) forming a mixture comprising at least one compound selected from the group consisting of perfluoroalkanesulfonyl fluorides and perfluorocycloalkanesulfonyl fluorides, up to an essentially stoichiometric amount of at least one fluoroether-monosubstituted carbinol, and triethyl amine; and (b) allowing said mixture to react in the absence of solvent at a temperature in the range of from about −20° C. to about 0° C.

* * * * *